United States Patent [19]

Mutschler et al.

[11] Patent Number: 5,124,326
[45] Date of Patent: Jun. 23, 1992

[54] PHARMACEUTICALLY EFFICACIOUS PTERIDINE DERIVATIVES

[75] Inventors: Ernst Mutschler, Mainz-Hechtsheim; Angelika Christner, Bickenbach; Ingrid Hofmann, Frankfurt am Main, all of Fed. Rep. of Germany

[73] Assignee: Roehm GmbH Chemische Fabrik, Darmstadt, Fed. Rep. of Germany

[21] Appl. No.: 513,001

[22] Filed: Apr. 20, 1990

[30] Foreign Application Priority Data

Apr. 21, 1989 [DE] Fed. Rep. of Germany ....... 3913142

[51] Int. Cl.⁵ .................. A61K 31/495; C07D 475/08
[52] U.S. Cl. ................................. 514/234.2; 514/249; 544/118; 544/249; 558/408; 558/401; 558/388; 546/230
[58] Field of Search ................ 544/260, 118; 514/249, 514/234.2

[56] References Cited

U.S. PATENT DOCUMENTS

| | | | |
|---|---|---|---|
| 3,081,230 | 3/1963 | Weinstock et al. | 514/258 |
| 4,252,809 | 2/1981 | Knauf et al. | 544/260 |
| 4,621,085 | 11/1986 | Borchard | 514/249 |
| 4,874,763 | 10/1989 | Hofmann et al. | 544/260 |
| 4,910,203 | 3/1990 | Rietzel et al. | 544/260 |

FOREIGN PATENT DOCUMENTS

| | | |
|---|---|---|
| 0059524 | 9/1982 | European Pat. Off. |
| 1620667 | 8/1970 | Fed. Rep. of Germany |
| 3407695 | 9/1985 | Fed. Rep. of Germany |
| 3412765 | 10/1985 | Fed. Rep. of Germany |
| 3740441 | 6/1989 | Fed. Rep. of Germany |
| 1599881 | 9/1981 | United Kingdom |

OTHER PUBLICATIONS

Endo, "Topics in Current Chemistry" vol. 128, pp. 100-103 (1985).

Primary Examiner—Donald G. Daus
Attorney, Agent, or Firm—Oblon, Spivak, McClelland, Maier & Neustadt

[57] ABSTRACT

A pharmaceutically efficacious pteridine compound of formula I:

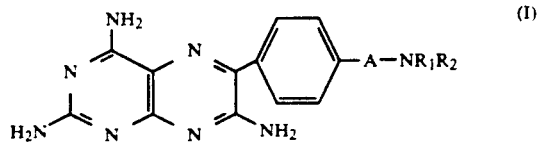

wherein A denote a bridging hydrocarbon group containing 1 to 8 carbon atoms and containing a

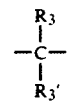

group directly bonded to the phenyl group and one of the methylene radicals of the bridging A group is optionally replaced by —O—; $R_1$ is hydrogen, a cycloalkyl group with up to 7 carbon ring atoms, or an alkyl group having 1 to 6 carbon atoms, benzyl, or aryl; $R_2$ is hydrogen or an alkyl group having 1 to 6 carbon atoms, or wherein $R_1$ and $R_2$ together form a five- or six-membered heterocyclic group which optionally contains additional hetero atoms selected from the group consisting of nitrogen, oxygen, and sulfur; $R_3$ is hydrogen or an alkyl group having 1 to 3 carbon atoms; $R_3'$ is hydrogen, an optionally substituted alkyl group having 1 to 3 carbon atoms, carboxyl, hydroxyl or $R_3$ and $R_3'$ together with the carbon atom to which they are attached form a cycloalkyl group and the pharmaceutically acceptable acid addition salts thereof.

6 Claims, No Drawings

PHARMACEUTICALLY EFFICACIOUS PTERIDINE DERIVATIVES

BACKGROUND OF THE INVENTION

1. Field of the Invention

The present invention relates to pharmaceutically active pteridine derivatives, which have an antiarrhythmic, diuretic and cardioprotective efficacy.

2. Discussion of the Background

Specific classes of substances with the pteridine structure have proven to be pharmaceutically efficacious. In pharmaceutical practice the 2,4,7-triamino-6-phenylpteridine (Triamterene) plays a prominent role as an anti-potassium uretic drug (U.S. Pat. No. 3,081,230: cf. E. Mutschler and H. Knauf, 30 Jahre Triamteren, Wissenschaftsverlag Koln, 1984). Broad-scale investigations have been devoted to the correlation between the structure and the effect in the pteridine class. Thus, Weinstock and Wiebelhaus investigated more than 500 pteridine derivatives. (Cf. K. Fellinger, Therapie mit Triamteren 21). However, with respect to their general acceptance, the conclusions that were drawn have not remained unrefuted. (Cf. E. Mutschler et al., loc. cit., pp. 11-18). The original concept, that compounds having the groups that are sterically less demanding, is no longer valid since it has now been shown that Triamterene derivatives which are substituted in the para position of the phenyl ring with a hydrophilic group have pharmaceutical utility (cf. U.S. Pat. No. 4,118,492, DE-A pharmaceutical agents are known as disclosed in U.S. Pat. No. 4,621,085 and/or the DE-A 34 12 765 which contain, as the active substance, a Triamterene derivative, whose 6-phenyl group is substituted lipophilically in the para position. Fluorine, chlorine, branched or cyclic alkyl having 3 to 6 carbon atoms, the benzyl-, trifluoromethyl or the nitro groups are cited as such lipophilic substituents.

German patent application p 37 40 441 (unpublished) shows compounds which are substituted para benzyltriamterene which has substituents both on the benzyl ring and at the benzylic carbon atom. The teaching of this application, however, does not point beyond the use of substituted derivatives of benzyltriamterene. If this prior art information is combined, the finding of G. H. Mudge (in Goodman-Gilman, The Pharmacological Basis of Therapeutics, 5th ed. McMillan Publishing Co., p 838) on the topic of Triamterene can still claim to be valid today: "It is a pteridine compound related chemically to folic acid. The diuretic activity of closely related homologues of Triamterene has been established but no specific structural requirements have been established."

Despite the excellent efficacy of some pharmaceutical active substance belonging to the pteridine class (This applies in particular to the Triamterene), there has still been a demand for active substances, which, with preferably greater hydrophilicity, maintain a therapeutic index that is at least just as good as Triamterene. Furthermore, it has been desirable to reduce the quantity of foreign substances subject to different metabolic processes and introduced to the organism. Correspondingly the goal has been to provide compounds useful in the smallest possible concentrations which exhibit a minimum of side effects. In addition, the related metabolic processes should be transparent and the secondary effects should be as straightforward and safe as possible.

SUMMARY OF THE INVENTION

Accordingly, one object of the present invention is to provide pteridine compounds which exhibit an effective therapeutic effect on a variety of disorders, while exhibiting a minimum of side-effects.

Briefly, the object and other objects of the present invention as hereinafter will become more readily apparent can be attained by a pteridene compound having the formula:

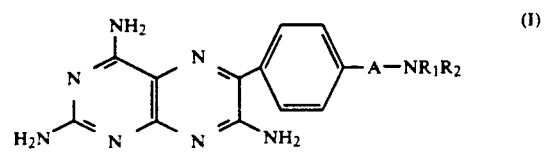

wherein A denotes a bridging hydrocarbon group containing 1 to 8 carbon atoms and contains a

group directly bonded to the phenyl group and one of the methylene radicals of the bridging A group may be replaced by —O—; $R_1$ is hydrogen or a cycloalkyl group with up to 7 carbon ring atoms, an alkyl group having 1 to 6 carbon atoms, benzyl, or aryl; $R_2$ is hydrogen or an alkyl group having 1 to 6 carbon atoms, or wherein $R_1$ and $R_2$ together form a five-or six-membered heterocyclic group which optionally contains additional hetero atoms selected from the group consisting of nitrogen, oxygen, and sulfur; $R_3$ is hydrogen or an alkyl group having 1 to 3 carbon atoms; $R_3'$ is hydrogen, an optionally substituted alkyl group having 1 to 3 carbon atoms, carboxyl, hydroxyl or $R_3$ and $R_3'$, together with the carbon atom to which they are attached form a cycloalkyl group, and the pharmaceutically acceptable acid addition salts thereof.

The present compound embraces all chiral configurations which substituent A may introduce into the molecule.

DETAILED DESCRIPTION OF THE PREFERRED EMBODIMENTS

In the formula above, the $R_3'$ substituent includes the OH group and amino groups. Further, radical A represents a —$CR_3R_3'$—$(CHR_3R_4)n$ group, wherein n is zero or a number from 1 to 7 or is a cycloalkyl group, in particular a cyclohexyl group. $R_4$ stands preferably for hydrogen or for an alkyl group having 1 to 4 carbon atoms or for an —$OR_5$ group wherein $R_5$ denotes hydrogen or an alkyl group having 1 to 4 carbon atoms provided that, when $n>1$, $R_4$ can assume different meanings. Preferably, the A group does not have a —$NR_1R_2$ group and an OH group at the same carbon atom. The bridging radical A preferably has the formula:

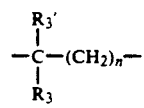

wherein $R_3$ or $R_3'$ has the above specified meanings and n is a number from 1 to 7. Preferably A is —$CH_2$—, —$CHOH(CH_2)_n$— or a

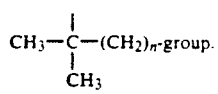

The $R_1$ and $R_2$ groups form, optionally with one or more heteroatoms, a five-or six membered ring. Preferably these groups form (non-aromatic) heterocyclic radicals containing one or two heteroatoms. Suitable examples of such heterocyclic groups include

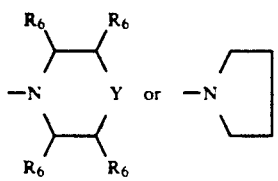

wherein Y is >$CHR_7$, —O—, or >$NR_8$, $R_6$ is hydrogen or alkyl having 1 to 4 carbon atoms; $R_7$ and $R_8$ is hydrogen or alkyl having 1 to 6 carbon atoms or benzyl.

The aromatic group Ar includes a phenyl or naphthyl group which is substituted, if necessary, with a $C_1$-$C_4$ alkyl group.

Pharmacologically acid addition salts of the present compound include, for example, salts of d-tartaric acid, maleic acid, fumaric acid, succinic acid, citric acid, cinnamic acid, salicylic acid, adipic acid, acetic acid, proprionic acid, p-aminobenzoic acid, methanesulfonic acid, sulfuric acid, and phosphoric acid, in particular the hydrochlorides and lactates.

The preparation of the compounds of formula (I) can be conducted by conventional methods, in particular in accordance with the Triamterene synthesis of R.G.W. Spickett and G.M. Timmis in J. Chem. Soc. 2887 (1954). This synthesis involves a ring closure reaction of a substituted benzyl cyanide of the formula II,

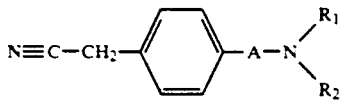

wherein $R_1$ and $R_2$ have the above described meanings, with 2,4,6-triamino-5-nitrosopyrimidine under conditions that are suitable for condensation. These conditions include e.g. the reaction of compound II with the nitrosopyrimidine under base catalysis in a suitable solvent, for example, an alcohol, in particular an ether alcohol such as 1-methoxy-2-propanol. A suitable base is, e.g., an alkali alcoholate, produced by dissolving an alkali metal, in particular sodium, in the alcohol. Normally a compound of formula II is used in only negligible excess relative to the 2,4,6-triamino-5- nitrosopyrimidine (TNP) reactant. Preferably, the reaction is conducted while heating, for example, at approximately 70°-120° C., preferably up to the boiling point of the alcohol, i.e. under reflux. Generally a reaction period of several hours suffices with about 2 hours being a sufficient time.

In isolating the product the reaction mixture is cooled to room temperature and then it is advantageous to initiate precipitation of the product by adding a solvent.

The precipitation can be completed by letting the mixture stand, for example at temperatures below room temperature.

The compound of formula I can be purified in the conventional manner, for example, by converting it to an acid addition salt, for example, by means of an aqueous acid solution. The salt in dissolved by heating to the boiling point, and then if necessary treating the hot solution with activated carbon. The solution is then allowed to cool to crystallize the salt.

The acid addition form of the compound of formula I can be neutralized by treatment with a suitable, preferably aqueous base, e.g. by means of concentrated ammonia.

The yields vary. They can however, be greater than 90% of the theoretical yield.

As a rule, the compounds of formula I yield crystals. Their purity can be tested, for example, by means of thin-layer chromatography. The compounds exhibit florescence in ultraviolet light that is typical for pteridine derivatives, a feature that can be used, e.g. for identification in chromatography.

NMR data and ultimate analysis confirm the above specified structure.

The compounds of formula II can also be prepared in the conventional manner.

The compounds of formula II can be prepared, for example, by reacting a compound of formula III,

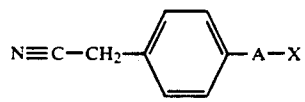

wherein A has the above described meaning and wherein X stands for a suitable leaving group such as Br, Cl, tosyl with an amine of the formula $HNR_1R_2$. If A stands, for example for a —$CH_2$— group, the introduction of the X group can also be attained in the conventional manner from 4-methylbenzylcyanide, for example through bromination with N-bromosuccinimide.

Compounds of formula II, wherein A stands for —($CH_2$)—, are obtainable with relatively few problems. Thus, starting with compounds of formula V:

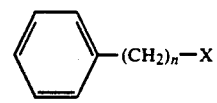

wherein n and X have the above described meanings, the compound IV:

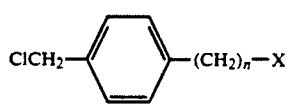

which reacts very selectively with NaCN to give the compound of formula III, can be prepared through chloromethylation, for example, by means of trioxane/HCl.

The compounds of the formula II, wherein $R_3$ stands for an OH group, can be obtained, for example, by reduction of a compound of formula VI with sodium borohydride, e.g. at room temperature in dioxane:

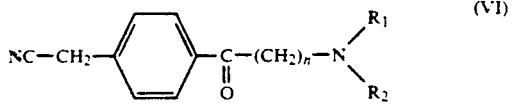

(VI)

wherein, $R_1$ and $R_2$ have the described meanings.

The compound of th formula VI can be prepared by reacting benzyl cyanide with an acid chloride of formula VII:

(VII)

wherein n and X have the designated meanings e.g. by heating in carbon disulfide followed by reaction with the amine $HNR_1R_2$.

On the whole, compounds of the formula I having the corresponding meanings for A, wherein n stands for 1 to 3, are of special interest. In particular they are compounds of the formula I with $A=(CH_2)_n$, wherein n is 1 to 3. Special importance is attributed to compounds in which $-NR_1R_2$ is a dialkyamino group or a benzylalkyalimo group, preferably alkyl- or benzyl substituted piperidino, morpholino, pyrrolidono or homopiperidino. Furthermore, compounds wherein

in A is —CHOH—, for —$CHC_6H_5$— and for —$C(CH_3)_2$— are of special interest. Examples include the following in their base form and the acid addition salts thereof:

2,4,7-Triamino-6-[4-(dimethylaminomethyl) phenyl]-pteridine. (compound IA)

2,4,7-Triamino-6-[4-(2-dimethylaminoethyl) phenyl]-pteridine. (compound IJ)

2,4,7-Triamino-6-[40(3-dimethylaminopropyl) phenyl]-pteridine. (compound IH)

2,4,7-Triamino-6-[4-(N-benzyl-N-isopropylaminomethyl) phenyl]pteridien. (compound IC)

2,4,7-Triamino-6-[4-(piperidinomethyl) phenyl]pteridine. (compound ID)

2,4,7-Triamino-6-[4-(4-benzylpiperidinomethyl) phenyl]pteridine. (compound IB)

2,4,7-Triamino-6-[4-(4-methylpiperidinomethyl)phenyl]pteridine. (compound IE)

2,4,7-Triamino-6-[4-(2,6-dimethylpiperidinomehyl) phenyl]pteridine. (compound IF)

2,4,7-Triamino-6-[4-(3,5-dimethylpiperidinomethyl) phenyl]pteridine. (compound IG)

2,4,7-Triamino-6-[4-(2-dimethylamino-1-hydroxyethyl)phenyl]pteridine. (compound IK)

2,4,7-Triamino-6-[4-(3-(2,6-dimethylpiperidino) propyl)phenyl]pteridine. (compound IL)

2,4,7-Triamino-6-[4-(3-(3,5-dimethylpiperidino) propyl)phenyl]pteridine. (compound IM)

2,4,7-Triamino-6-[4-(4-dimethylaminocyclohexyl) phenyl]pteridine. (compound IN)

The compounds of formula I of the invention have pharmaceutical, in particular cardioprotective, antiarrhythmic and diurectic, properties, and in particular anti-potassium uretic efficacy. They are characterized in general by their good solubility behavior in an aqueous milieu. The acid addition compounds of formula (I) are also readily soluble.

Antiarrhythmic Effect

The suitability of the present compound as an antiarrhythmic active substance can be determined by researching a prototype. One suitable test method is, for example, that of V. Borchard, R. Bosken, and K. Greef, Arch. intern. Pharmacodyn. Therap., 256, (2), 253 (1982) with which arrhythmia or asystolia were induced by means of a 50 Hz alternating current at the isolated left vestibulum and at the right, ventricular papillary muscle of the guinea pig.

Diuretic and potassium-economizing Effect

The compounds of formula I and their acid addition salts, with physiologically tolerable acids are quite suitable for peroral and intravenous medication. The diuresis tests were conducted according to the following method.

Diuresis Tests/Method

Male Wister rats, weighing approximately 130 g, were used in the tests. Food had been withdrawn from the rats for 18 hours. Immediately before the intravenous administration of the test substance, they were fed orally a quantity of 20 ml/kg of 0.9% NaCl solution. The intravenous medication ranged from 0.1 to 250 μmol of the active substance per body weight in 4 ml/kg of 0.9% NaCl solution (pH 3). Under a slight anesthesia, administration was by the caudal vein. Generally six experimental animals were used per test. The peroral administration was by means of probang in the gastrointestinal region. The substances were administered in a mixture comprising Tylose ® and physiological NaCl solution, which serves simultaneously as the hydration agent (20 ml/g KG). The animals were placed individually into diuresis cages and urine was collected after 2.5 or 3 or 6 hours. The electrolytes ($Na^+$ $K^+$, $Mg^{+2}$) were determined by means of flame photometry and by means of atomic absorption measurement with the FL6 automatic electrolyte equipment from Zeiss/Oberkochen.

Curves for dose/response correlations were obtained with the aid of non-linear regression analysis with the NONLIN computer program by C. Daniel and F. S. Wood in "Fitting Equations to Data", J. Wiley & Sons, New York, 1980.

Thus, the characteristic value $ED_{50}$ (=potency) applied to determine the diuretic efficacy is defined as the quantity of active substance per kg of body weight, which is necessary for the semi-maximum effect.

The renal recovery of the test substances serves as a means of measuring resorption following oral administration. The resorption rate is determined from the quotients of the recovery rates following peroral (p.o.) and intravenous (i.v.) administration, as given in percent. The recovery rate notes the renally excreted quantity based on the medicated quantity of the active substances. The concentration of the test substances in the urine of the animals is determined in accordance with thin-layer chromatographic separation by means o spectrophotometry.

The IE compound shows, for example in comparison to Triamterene:

i) A higher potassium-saving potency following peroral administration;

ii) A 6.5-fold increased solubility (pH 7.4 in phosphate buffer);
iii) No metabolization.

TABLE 1

| Compounds of formula I | lipophilicity log P (ph = 7.4) | solubility mg/l (ph = 7.4) | melting or decomtion point | resorption rate | Na$^+$/ K$^+$ i.v. | quotient p.o |
|---|---|---|---|---|---|---|
| IA | −0.36 | 580 | 308 | 11% | 9 | 18 |
| IB | 2.70 | 1.1 | 235 | <1% | 17 | 4 |
| IC | 3.20 | 1.9 | 234 | (1) | 7 | 13 |
| ID | 0.20 | 76 | 270 | 19% | 37 | 7 |
| IE | 0.89 | 139 | 300 | 31% | 27 | 14 |
| IF | 0.68 | 25 | 299–303 | 33% | 21 | 15 |
| IG | 1.74 | 13 | 312 | 23% | 39 | 7 |
| IH | −0.60 | 2000 | 242 | 3% | 12 | 7 |
| IJ | −0.59 | 2200 | 247 | 4% | 10 | 6 |
| IL | 0.04 | 1500 | 269 | 3% | 170 | 8 |
| IM | 1.18 | 135 | 264 | 7% | 128 | 27 |
| Triamterene | 1.26 | 21 | 325 | (ca. 80%) | 8 | 6 |

(1) is metabolized quantitatively

TABLE II

| | Correlation between dose and effect for the active substance of formula I (μmol/kg) | | | | | | | |
|---|---|---|---|---|---|---|---|---|
| active substance | i.v. duration | urine volume | Na$^+$ | K$^+$ | duration | Na$^+$ | p.o. urine volume | K$^+$ |
| IH | 2.5 h | 1.23 | 1.44 | 1.41 | | | | |
| | 6 h | 1.70 | 1.83 | 1.30 | | | | |
| IJ | 2.5 h | 2.36 | 1.63 | 1.04 | | | | |
| | 6 h | 2.61 | 1.64 | 2.60 | | | | |
| IE | 2.5 h | 2.65 | 3.13 | 5.40 | 3 h | 11.80 | 9.49 | 2.16 |
| | 6 h | 8.24 | 12.72 | 5.90 | 6 h | 14.77 | 12.72 | 2.41 |
| Triamterene | 2.5 h | 13.94 | 2.38 | 11.15 | 3 h | 6.40 | 6.17 | 3.38 |
| | 6 h | 10.62 | 10.55 | 9.79 | 6 h | 6.57 | 5.06 | 8.39 |

The high potency of the compounds of the present invention permits a relatively small dose of an active substance of formula I of the invention, wherein, of course, weight, age, constitution and the general state of health of the patient must be taken into consideration. Generally a daily dose of 0.2 to 200 mg, preferably 5 to 50 mg, is suitable. The substance can be administered in several units, for example 5 mg each twice daily. It can be administered orally or parenterally.

The active substances of formula I are quite suitable as drugs having a diuretic, anti-potassium uretic, anti-magnesium uretic, anti-hypertensive, antiarrhythmic and cardioprotective effect. They are also specially suitable when combined with other active substances having comparable indication, provided they are compatible. The combination with fast acting diuretics such as Furosemide (4-chloro-N-furfuryl-5-sulfamoylanthranilic acid according to U.S. Pat. No. 3,058,882) is of considerable importance.

It must be stressed that the potassium uretic action of Furosemide can be compensated for with approximately one-third to one-tenth of the dose of an active substance of formula I. Generally the quantities to be administered are in a ratio of 0.25 to 100 parts by weight of Furosemide to 1 part by weight of the active substance of formula I. With a recommended daily dose of twice 40 mg of Furosemide administered perorally, it is recommended that 8 mg of the active substance of formula I be administered. An intravenous administration of 20 mg of Furosemide corresponds to the intravenous administration of 2 mg of the active substance of formula I.

Of special interest is also the combination with calcium-antagonistic active substances as also described in DE-OS 26 58 500, in particular Verapamil, Gallopamin, Nifedipine and Diltiazem. In the combined preparations the ratio of the calcium antagonists to the active substance of formula I is by weight 100:1 to 0.1:1.

Of special interest is also the combination of the potassium-saving active substances of formula I with other diuretics. (Cf. Ullmans Encyclopädie der technischen Chemie, 4th edition, Vol. 10, pp. 181–186, Verlag Chemie, 1975).

Saluretics, in particular the benzothiadiazine derivatives such Chlorothiazide, Hydrochlorothiazide and the Hydrochlorothiazide analogues, in particular Hydroflumethiazide, Thiabutazide, Bendroflumethiazide, Trichloromethiazide, Methylcyclothiazide, Polythiazide, Cyclothiazide, Cyclopenthiazide, Ethiazide, Benzothiazide, Methylbenzylhydrochlorothiazide, also the sulfamoyl salurectics such as Chlorothalidon, Mefruside, Clopamide. Quinethazone, and Chlorexolon can be used in combination.

In this case the ratio of the active substances of formula I, e.g. the active substances of formula IE to the doses recommended for the individual diuretic is by weight 2:1 to 0.01:1.

In particular, note is taken of the combination with Hydrochlorothiazide, wherein the proportion by weight of the active substance of formula IA to the saluretic ranges from 2:1 to 0.05:1.

Furthermore, the active substance of formula I is suitable to combine with β blockers analogous to those preparations that are combined with Triamterene as taught in GB-PS 1,584,089, in particular combined with propranolol or its acid addition salts. Saluretics can also be included in the combination. In this case the ratio of the active substances of formula I to the β blockers by weight is preferably 2:D to 10 D, wherein D denotes the recommended daily dose up to minus 50% of the recommended daily dose.

The pharmaceutical preparation containing the new active substance of formula I can be manufactured in the conventional manner, and they can contain the usual carrier and auxiliary substances. One embodiment of the invention is solid preparations that are suitable for oral administration such as pills, capsules, tablets, and th like. For oral application pharmaceutically indifferent solids such as mannitol, lactose, organic and inorganic calcium salts, etc. can be used as the carrier materials. Suitable binders are, among others, polyvinyl pyrrolidone, gelatin and cellulose derivatives. Such agents which explode tablets as starch or alginic acid, lubricants such as stearic acid or its salts and inorganic flow agents such as talcum or colloidal silicic acid and taste correctors etc. can be used as other additives.

The active substances can be mixed with auxiliary agents in the conventional manner and granulated in th wet or dry state. Depending on the type of additives used, a powder that can be directly made into tablets can also be obtained, if necessary, by simple blending. The granules or powder can be filled directly into capsules or compressed in the conventional manner into tablet cores. In the case of parenteral administration the therapeutic drugs can also be prepared and administered in the conventional manner.

Having now fully described the invention, it will be apparent to one of ordinary skill in the art that many changes and modifications can be made thereto without departing from the spirit or scope of the invention as set forth herein.

The following example serves to explain the preparation of the compounds of formula I and the manufacture of the pharmaceutical preparations.

EXAMPLES

A. The following examples serve to explain the manufacture of the pharmaceutical preparations.

Tablets can be manufactured in the following manner:

A mixture comprising:

| | |
|---|---|
| active substance of formula I | 16.67 kg |
| lactose | 54.32 kg |
| cellulose powder | 15.00 kg |
| talcum | 5.08 kg |
| corn starch | 2.91 kg |
| calcium carbonate | 2.50 kg |
| calcium carboxymethyl cellulose | 1.81 kg |
| magnesium stearate | 0.74 kg |
| polyvinyl pyrrolidone (25,000) | 0.52 kg |
| highly disperse silicon dioxide | 0.45 kg | is compressed to form tablet cores.

B. The following examples serve to explain the preparation of the compounds. The prestages are identified by means of gas chromatography/mass spectroscopy. The compounds of formula I of the invention are identified by NMR and ultimate analysis.

1. Preparation of the compounds of formula I 1.1. Preparation of
2,4,7-triamino-6-[4-(dimethylaminomethyl)-phenyl]-pteridine (compound of formula IA)

| Feedstock: | | |
|---|---|---|
| 23 mMol | dimethylaminomethylbenzylcyanide | 4.0 g |
| 22 mMol | sodium | 0.5 g |
| 29 mMol | 2,4,6-triamino-5-nitrosopyrimidine (TNP) | 2.9 g |
| 128 ml | 1-methoxy-2-propanol p.a. | |

In a 250 ml round bottomed, three necked flask with condenser and drying tube (with self-indicating silica gel) 0.5 g of sodium are dissolved in 78 ml of 1-methoxy-2-propanol. To this 2.9 g of TNP and a solution of 4.0 g of dimethylaminomethylbenzylcyanide in 50 ml of 1-methoxy-2-propanol are added. The reaction mixture is heated at reflux for 2 hours, cooled to room temperature and left at +4° C. for 12 hours. The precipitated material is filtered off by suction through a D-4 glass filter funnel and washed with acetone, and dried in a vacuum drying oven for 18 hours at 60° C.

Yield: 4.6 g = 78% of the theoretical yield

The raw product is recrystallized with 160 ml 1N hydrochloric acid and 1.5 g of activated carbon. The activated carbon is separated by means of plaited filters and membrane filters (0.2μ). The solution is cooled slowly and stored overnight at +4° C. The yellow precipitate is filtered by suction by means of a D4 glass filter funnel and washed with acetone. The product is dried in a vacuum drying oven for 6 hours at 60° C. and for 5 hours at 105° C.

Yield: 4.5 g = 65% of the theoretical yield.

Loss on drying (105° C.5 hours/$P_2O_5/10^{-1}$ torr) 2.0%; $C_{15}H_{20}N_8Cl_2$, MW:383.28, flash point (decomposition) 308° C.

| | C | H | N | Cl |
|---|---|---|---|---|
| calculated | 47.0% | 5.3% | 29.2% | 18.5% |
| found | 46.5% | 5.4% | 28.8% | 17.9% |

1.2. Preparation of
2,4,7-triamino-6-[4-(4-benzylpiperidinomethyl)phenyl]-pteridine (compound IB):

| Feedstock: | | |
|---|---|---|
| 24.0 mMol | 4-(N-benzylpiperidinomethyl)benzylcyanide | 7.3 g |
| 21.0 mMol | 2,4,6-triamino-5-nitrosopyrimidine (TNP) | 3.4 g |
| 22.0 mMol | sodium | |
| 130.0 ml | 1-methoxy-2-propanol | 0.51 g |

In a 250 ml round-bottom flask, 0.51 g of sodium are dissolved in 70 ml of 1-methoxy-2-propanol. To this 2,4 g of TNP, 7.3 g of 4-(N-benzylpiperidinomethyl) benzylcyanide and 60 ml of 1-methoxy-2-propanol are added and heated at reflux for 2 hours. The feedstock is cooled to room temperature and stored at +4° C. for 16 hours. The precipitate is filtered by suction over a D4 glass suction funnel, washed with 30 ml of 1-methoxy-2-propanol, 300 ml of acetone and 100 ml of diethyl ether and dried in a vacuum drying oven at 60° C. for 2 hours. The raw product (4.8 g, 50%) is recrystallized from 960 ml of boiling 1N hydrochloric acid using 1.5 g of activated carbon. The flask is allowed to stand for 5 hours at 22° C. and for 18 hours at 4° C. The precipitate is filtered by suction over a D4 glass filter funnel and rinsed with water in a round bottom flask. This suspension is set to pH 10 with concentrated ammonia and stirred at 22° C. for 18 hours. The precipitate is filtered by suction over a D4 glass filter funnel, washed with water and acetone and dried in a vacuum drying oven for 10 hours at 60° C. and for 5 hours at 105° C.

Yield: 3.25 g = 34% of the theoretical yield

|  | C | H | N |
|---|---|---|---|
| calculated | 68.3% | 6.2% | 25.5% |
| found | 66.7% | 6.3% | 24.9% |
| corrected for H₂O | 67.6% | | | decomposition point 235° C.
solubility in isotonic phosphate buffer pH 7.4, 1.1 mg/l The following compounds of the formula I are also prepared in the same manner as example 1.2

1.3.
2,4,7-Triamino-6-[4-(N-benzyl-N-isopropylaminomethyl)phenyl]pteridien (compound IC)

Yield: =34% of the theoretical yield 1.4. 2,4,7-Triamino-6-[4-(piperidinomethyl)phenyl]pteridine (compound ID)

Yield:=59% of the theoretical yield 1.5.
2,4,7-Triamino-6-[4-(4-methylpiperidinomethyl)phenyl]pteridine (compound IE)

Yield:=51% of the theoretical yield 1.6. 2,4,7-Triamino-6-[4-(2,6-dimethylpiperidinomehyl)phenyl]pteridine (compound IF)

Yield: =19% of the theoretical yield 1.7. 2,4,7-Triamino-6-[4-(3,5-dimethylpiperidinomethyl)phenyl]pteridine (compound IG)

Yield: =52% of the theoretical yield 1.8. Preparation of
2,4,7-Triamino-6-[40(3-dimethylaminopropyl)phenyl]-pteridine (compound IH)

Feedstock:
0.8 g=32.6 mMol sodium
7.2 g=35.6 mMol 4(3-dimethylaminopropyl) benzylcyanide
5.0 g=32.3 mMol 2,4,6-Triamino-5-nitrosopyrimidine (TNP)
194.0 g 1-methoxy-2-propanol In a 500 ml round-bottomed, two necked flask, 0.8 g of sodium are dissolved in 94 ml of 1-methoxy-2-propanol. To this 7.2 g of 4-(3-dimethylaminopropyl) benzylcyanide and 5.0 g TNP are added. The containers are rinsed with 100 ml of 1-methoxy-2-propanol. The feedstock is heated at reflux for 2 hours, cooled to room temperature and stored at +4° C. for 18 hours. The material which precipitates is filtered by suction over a D4 glass filter funnel and discarded. While stirring, the filtrate is treated with 600 ml diethyl ether and stirred at +15° C. for 4 hours. The compound which precipitates is filtered by suction over a D4 glass filter funnel and washed with 200 ml of diethyl ether. The residue is dried in a vacuum drying oven (oil pump) at 602 C. for 18 hours. The raw product is heated to boiling with 180 ml ethanol and to this 116 ml 1N hydrochloric acid is slowly added. After boiling for a short period of time, the solution, is filtered by means of a plaited filter and cooled to room temperature. The flask is left to stand at +4° C. for 18 hours. The precipitate is filtered by suction by means of a D4 glass filter funnel, rinsed with 250 ml of distilled water in a round bottomed flask, set at pH 10 with concentrated ammonia, and stirred at +25° C. for 18 hours. The compound which precipitates is filtered by suction by means of a D4 glass filter funnel, washed with 50 ml of distilled water and 300 ml of acetone. The product is dried in a vacuum drying oven (oil pump) for 18 hours at 60° C. and 5 hours at 105° C.

Yield: 4.5 g=41.3% of the theoretical yield.

|  | C | H | N | DC |
|---|---|---|---|---|
| calculated | 60.3% | 6.6% | 33.1% | |
| found | 59.6% | 6.5% | 33.2% | >99% | decomposition temperature: 242° C.
solubility in isotonic phosphate buffer pH 7.4:2,000 mg/l distribution coefficient: log P− −0.60 triple analysis).

1.9 Preparation of
2,4,7-Triamino-6-[4-(2-dimethylaminoethyl)phenyl]-pteridine. (compound IJ)

Feedstock:
0.5 g=22.4 mMol sodium
4.6 g=24.4 mMol 4-(2-dimethylaminoethyl) benzylcyanide
3.4 g=133.2 mMol 1-methoxy-2-propanol The settled and the precipitated material are worked up together.

Raw product: 4.3 g

The raw product is heated in 130 ml of boiling hydrochloric acid containing 1.4 g of activated carbon. The activated carbon is separated by means of plaited filters and membrane filters (0.2μ). The solution is cooled to room temperature and stored at +4° C. for 5 hours. The precipitate is filtered by suction by means of a D4 glass filter funnel and subsequently treated as 2,4,7-triamino-6-[4-(3-dimethylamino-propyl)phenyl]pteridine.

Yield: 2.4 g=68% of the theoretical yield.

|  | C | H | N | DC |
|---|---|---|---|---|
| calculated | 59.2% | 6.2% | 34.5% | |
| found | 58.3% | 6.2% | 34.5% | 98.9% | decomposition temperature: 247° C.; solubility in isotonic phosphate buffer pH 7.4:2,200 mg/l; distribution coefficient: log P= −0.59 (double analysis).

1.10. Preparation of
2,4,7-triamino-6-(4-[2-dimethylamino-1-hydroxyethyl)-phenyl]pteridine (compound IK)

Feedstock:
67.7 mMol sodium 1.5 g
57.0 mMol 2,4,6-triamino-5-nitrosypyrimidine (TNP) 8.8 g
68.5 mMol 4-(2-dimethylamino-1-hydroxyethyl) benzylcyanide 14.0 g
382.0 mMol 1-methoxy-2-propanol In a 750 ml of round bottomed, three necked flask, propanol. To this 8.8 g of TNP and a solution comprising 14.0 g of 4-(2-dimethylamino-1-hydroxyethyl)benzylcyanide in 182 ml of 1-methoxy-2-propanol are added. The reaction mixture is heated at reflux for 2 hours, cooled to room temperature and left for 12 hours at +4° C. The resulting precipitate is filtered by suction by means of a D4 glass filter funnel and washed with 1-methoxy-2-propanol. 0.2 g of a brown substance is discarded. The united filtrates are evaporated to dryness in a rotary evaporator (oil pump, 50° C. bath temperature) and treated with 1.5 l of diethyl ether. The precipitate is filtered off by suction by means of a D4 glass filter funnel and dried in a vacuum drying oven at 60° C. for 18 hours.

Yield: 24.6 g = 127% of the theoretical yield.

The raw product is recrystallized with 1,200 ml 1N hydrochloric acid and 8 g of activated carbon. The activated carbon is separated by means of plaited filters and membrane filters (0.2μ). The solution is left overnight at +4° C. The resulting yellow precipitate is filtered by suction by means of a D4 glass filter funnel, washed with 3×250 ml of acetone and dried in a vacuum drying oven for 18 hours at 60° C. and for 18 hours at 60° C. and for 5 hours at 105° C.

Yield: 16.9 g of the theoretical yield.

The recrystallization is repeated with 670 ml 1N-hydrochloric acid and 5.5 g of activated carbon.

Yield: 13.1 g = 67% of the theoretical yield of the feedstock TEt(OH)N(Me₂).2HCl.H₂O

|  | C | H | N | Cl |
|---|---|---|---|---|
| calculated | 44.6% | 5.6% | 26.0% | 16.4% |
| found | 45.6% | 5.6% | 26.1% | 16.2% |

1.11.
2,4,7-Triamino-6-[4-(3-(2,6-dimethylpiperidino)propyl)-phenyl]pteridine. (compound IL)

Feedstock:
0.32 g = 13.9 mMol sodium
2.1 g = 13.8 mMol 2,4,6-triamino-5-nitrosopyrimidine (TNP)
4.1 g = 15.2 mMol 4-[3-(3,5-dimethylpiperidino)propyl]-benzylcyanide
83.0 ml 1-methoxy-2-propanol In a 250 ml round bottomed flask, 0.32 g of sodium are dissolved in 43 ml of 1-methoxy-2-propanol. To this 2.1 g of TNP and 4.1 g of 4-[3-(3,5-dimethylpiperidino)-propyl]benzylcyanide are added. The containers are subsequently rinsed with 40 ml of 1-methoxy-2-propanol. The feedstock is heated at reflux for 2 hours, cooled to room temperature and stored for 18 hours at +4° C. The material which precipitates is filtered by suction by means of a D4 glass filter funnel, washed with 10 ml of 1-methoxy-2-propanol and 200 ml acetone and dried in a vacuum drying oven (oil pump) at 60° C. for 18 hours. The mother liquor and the acetone are evaporated to dryness in a rotary evaporator and stirred with 150 ml of acetone for 1 hour. The precipitate is filtered by suction by means of a D4 glass filter funnel and dried in the same manner as the first precipitate. Both are recrystallized together in 110 ml of boiling 1N hydrochloric acid containing using 1.3 g of activated carbon. The flask is slowly cooled and stored at +4° for 18 hours. The precipitate is filtered by suction by means of a D4 glass filter funnel, rinsed with distilled water in a round bottomed flask and set at pH 10 with concentrated ammonia. After 6 hours of stirring at room temperature, the precipitate is filtered by suction (D4), washed with distilled water, and dried in a vacuum drying oven (oil pump) for 18 hours at 60° C. and for 5 hours at 105° C.

Yield: 1.8 g = 32.1% of the theoretical yield.

|  | C | H | N |
|---|---|---|---|
| calculated | 65.0% | 7.4% | 27.6% |
| found | 63.8% | 7.3% | 26.8% |

Decomposition temperature: 264° C.
Solubility in isotonic phosphate buffer pH 7.4 = 135 mg/l
Distribution coefficient: log P±1.18 = 0.05

2. Preparation of substituted benzyl cyanides of formula (II)

2.1. Dimethylaminomethylbenzylcyanide

Feedstock:

| 39.0 mMol | 4-bromomethylbenzylcyanide | 8.2 g |
| 99.7 mMol | dimethylamine 40% | 12.7 ml |
| 453.0 ml | methanol | |

In a 1 liter round bottomed flask with condenser and thermometer 8.2 g of 4-bromomethylbenzylcyanide are dissolved in 453 ml methanol and cooled to +3° C. At this temperature 12.7 ml of 40% dimethylamine solution are added drop-by-drop. The solution is subsequently stirred for ¼ hour at +5° C. and 2 hours at room temperature. The reaction sequence is controlled by means of thin-layer chromatography (0.57 ml of specimen +0.43 ml methanol: eluent n-butanol: acetic acid: water = 4:1:1; v/v; 10 μl coating; HPTLC finished plated diatomaceous earth 60 F 254). Following removal of the volatile components is a rotary evaporator (20 torr, 40° C. bath temperature) the residue is absorbed in 20 ml 1N hydrochloric acid and extracted with a total of 150 ml of diethyl ether. The clear, aqueous phase is treated with 30 ml of 1N sodium hydroxide solution (ice cold) and extracted subsequently with 250 ml of diethyl ether. The organic phase is washed to neutrality with a saturated solution of common salt, dried with sodium sulfate and evaporated to dryness in a rotary evaporator (30° C. bath temperature, 20 torr).

Yield: 4.0 g = 58.8% of the theoretical yield 2.2. 4-(4-Benzylpiperidinomethyl)benzylcyanide Feedstock:

| 24.0 mMol | 4-bromomethylbenzylcyanide | 5.0 g |
| 48.0 mMol | benzylpiperidine | 8.4 g = 8.4 ml |
| 80.0 mMol | methanol p.a. (MeOH) | |

In a 250 ml round bottomed flask 5.0 g of 4-bromomethylbenzylcyanide are weighed in and 80 ml MeOH are added. The solution is cooled in an ice bath and 8.4 ml benzylpiperidine are added drop-by-drop after ¼ hour, the solution is stirred at +5° C. and then for 3½ hours at room temperature. The feedstock is concentrated by evaporation. The residue is treated with 50 ml 1N-hydrochloric acid and 20 ml of distilled water and shaken with 2×100 ml diethyl ether. This aqueous phase is treated with 70 ml 1N sodium hydroxide solution and extracted with 2×100 ml diethyl ether. This organic phase is washed to neutrality, dried with sodium sulfate and concentrated to dryness in a rotary evaporator.

The raw product (12 g) is purified by means of column chromatography (diatomaceous earth 60, grain size 0.063–0.200 mm/diethyl ether/250 ml of drop funnel).

Yield: 9.0 g of the theoretical yield.

The following compounds of formula (II) are prepared analogously to example 2.2.

2.3. Benzyl-isopropylaminomethyl-benzylcanide 2.4. (4-Piperidinomethyl)benzylcyanide 2.5. 4-(4-Methylpiperidinomethyl))benzylcyanide 2.6. 4-(2,6-Dimethylpiperidinomethyl)benzylcyanide 2.7. 4-(2,5-Dimethylpiperidinomethyl)benzylcyanide 2.8. 2-(3-Dimethylaminopropyl)benzylcyanide Feedstock:
25.8 g = 81.6 mMol 4-(3-chloropropyl)benzylcyanide
22.0 ml = 163.2 mMol 40% dimethylamine solution
26.0 ethanol In a 250 ml round bottomed flask 15.8 g of 4-(3-chloropropyl)benzylcyanide, 22.0 ml of 40% dimethylamine solution and 26 ml of ethanol are mixed and heated at reflux for 4 hours. The reaction mixture is connected by evaporation in a rotary evaporator. The residue is treated with 160 ml of 1N hydrochloric acid and extracted with 150+100 ml of diethyl ether. The aqueous phase is washed with 2×150 ml of diethyl ether, dried with sodium sulfate and evaporated to dryness in a rotary evaporator. The raw product (11.3 g) is purified by means of vacuum distillation (0.06 torr, 45° C. boiling temperature).

Yield: 7.2 g = 40.9% of the theoretical yield 2.9. 4-(2-Dimethylaminoethyl)benzylcyanide Feedstock:
9.7 g = 45.0 mMol 4-(2-chloroethyl)benzylcyanide
14.6 ml = 108.0 mMol 40% dimethylamine solution
10.4 ml ethanol
Conducted analogously to example 2.8

| reaction time: | 6 hours |
| --- | --- |
| raw product: | 5.3 g |
| vacuum distillation: | 0.06 torr/97° C. |
| Yield: | 4.6 g = 45.1% of the theoretical yield |

2.10.
4-(2-Dimethylamino-1-hydroxyethyl)benzylcyanide

| Feedstock: | | |
| --- | --- | --- |
| 98.9 mMol | dimethylaminoacetylbenzylcyanide | 20.0 g |
| 197.8 mMol | sodium hydridoborate | 7.6 g |
| 740.0 ml | dioxane | |
| 75.5 ml | distilled water | |

In a 2 liter round bottomed flask 20.0 g of dimethylaminoacetylbenzylcyanide are dissolved in 740 ml of dioxane. At 0° C. 7.6 g of sodium hydridoborate, dissolved in 75.5 ml of water, is added drop by drop. The temperature should not exceed +15° C. The reaction sequence is controlled by means of thin layer chromatography (0.20 ml specimen+0.30 ml of methanol). Eluting agent:chloroform:methanol:water=65:35:4 v/v, finished plates of diatomaceous earth 60 F 254). After 1 hour at room temperature the reaction mixture is treated with 142 ml 1N hydrochloric acid and concentrated by evaporation (bath temperature 50° C., water jet vacuum). 200 ml water and 50 ml 1N hydrochloric acid are added to the residue and extracted by shaking with a total of 1,100 ml of diethyl ether. The aqueous phase is treated with 250 ml of sodium chloride and extracted with a total of 1,100 ml of diethyl ether. The organic phase is washed to neutrality, dried with anhydrous sodium sulfate and evaporated to dryness in a rotary evaporator (30° C. bath temperature, water jet pump).

Yield: 14.3 g = 70.8% of the theoretical yield 2.11. 4-[3-(3,5-Dimethylpiperidino)propyl]benzylcyanide Feedstock:

| 5.3 g = | 27.4 mMol 4-(3-chloropropyl)benzylcyanide |
| --- | --- |
| 4.4 g = | 29.5 mMol sodium iodide |
| 6.2 g = | 7.4 ml = 54.8 mMol 3,5-dimethylpiperidine |
| | 32.9 ml acetone |

In a 250 ml round bottom flask 5.3 g of 4-(3-chloropropyl)benzylcyanide, 4.4 g of sodium iodide, 62.2 g of 3,5-dimethylpiperidine and 32.9 ml of acetone are mixed together and boiled for 1 hour at reflux.

The reaction mixture is concentrated by evaporation in a rotary evaporator. The residue is treated with 80 ml 1N-hydrochloric acid and 20 ml of water and extracted with 80×50 ml diethyl ether. The aqueous phase is treated with 80 ml 1N sodium hydroxide solution and shaken with 150 and 100 ml of diethyl ether. This organic phase is washed with 5×80 ml of water, dried with sodium sulfate and concentrated to dryness in a rotary evaporator.

Yield: 4.1 g = 55.4% of the theoretical yield

3. Preparation of the compounds of formula (III)

3.1.1 Bromomethylbenzylcyanide

Feedstock:

| 150 mMol | p-methylbenzylcyanide | 19.8 g = 19.8 ml |
| --- | --- | --- |
| 150 mMol | N-bromosuccinimide NBS | 26.7 g |
| 150 ml | carbon tetrachloride | 0.9 g |
| | dibenzoyl peroxide | |

In a 500 ml round bottomed, three-necked flask 26.7 g of NBS and 150 ml of carbon tetrachloride are added and heated at reflux under argon for 1 hour under reflux. The succinimide precipitate resulting from the reaction is filtered by suction by means of a D4 glass filter funnel and washed with 15 ml of carbon tetrachloride. The filtrate is concentrated by evaporation in a rotary evaporator (20 torr, 40° C. bath temperature). The residue is treated with 60 ml pentane and 60 ml of diethyl ether and cooled to −10° C. for 12 hours. The precipitated crystals are filtered by suction by means of a D4 glass filter funnel, washed with ether-pentane and dried at room temperature in a vacuum drying oven.

Yield: 7.8 g = 27.6% of the theoretical yield
eluting agent:toluene:acetic acid = 7:1

3.2. 4-(3-Chloropropyl)benzylcyanide

Feedstock:

| 18.2 g = | 89.6 mMol (4-chloromethylphenyl)3-chloropropane |
| --- | --- |
| 4.4 g = | 89.6 mMol sodium cyanide (NaCN) |
| 44.8 ml | 90% ethanol |

In a 100 ml of round bottomed two-necked flask 4.4 g of NaCN, 18.2 g of 1-(4-chloromethylphenyl)3-chloropropane and 44.8 ml of 90% ethanol are added and boiled at reflux for 5 hours. The feedstock is cooled to room temperature and the precipitate is filtered by suction. The filtrate is concentrated by evaporation. The residue is absorbed in 700 ml of diethyl ether, washed to neutrality with 2×250 ml of distilled water and dried with sodium sulfate. The solution is evaporated to dryness in a rotary evaporator.

Yield: 17.3 g = 100% of the theoretical yield.

3.3. 4-(2-Chloroethyl)benzylcyanide

Feedstock:
9.9 g = 52.4 mMol 1-(4-chloromethylphenyl)2-chloroethane
2.6 g = 52.4 mMol sodium cyanide 26.2 g ethanol (90%).
Conducted analogously to example 3.2.

| reaction time: | 4 hours |
|---|---|
| Yield: | 9.2 g = 95% of the theoretical yield |

3.4. 4-(3-Chloropropyl)benzylcyanide

Feedstock:
23.0 g = 90 mMol 4(3-chloropropyl)benzylchloride
3.1 g = 90 mMol sodium cyanide
32.0 ml ethanol 90%
Conducted analogously to example 3.2.
Yield: 12.7 g = 100% of the theoretical yield

4. Preparation of the compounds of formula IV

4.1. 4-(3-Chloropropyl)benzylchloride

Feedstock:

| 20.0 g = | 19.1 ml | 129.3 mMol 3-phenylpropylchloride |
|---|---|---|
| 5.2 g = | | 56.8 mMol 1,3,5-trioxane |
| 6.8 g | | 48.8 mMol phosphorus pentoxide ($P_2O_5$) |
| 19.2 g = | 16.8 ml | concentrated hydrochloric acid |
| 17.6 g = | 10.4 ml | o-phosphoric acid 85% |
| | 15.6 ml | |

In a 100 ml round bottom flask 19.1 ml of 2-phenylpropylchloride, 5.2 g of 1,3,5 trioxane, 6.8 g of $P_2O_5$, 16.8 ml of concentrated hydrochloric acid are added together and heated to 80° C. Dry HCl gas is introduced for 4.5 hours. After 23 hours of reaction time, the feedstock is cooled to room temperature and put on ice. The aqueous phase is extracted with 2×200 ml of diethyl ether. The organic phase is washed with 2×200 ml of distilled water, 2×150 ml of saturated sodium hydrogen carbonate solution and once again with 2×150 ml of distilled water and dried with potassium carbonate. The solution is evaporated to dryness in a rotary evaporator. The raw product is purified by vacuum distillation (0.05 torr, boiling point: 99°).

Yield: 14.8 g = 56.3% of the theoretical yield

4.2. 4-(2-Chloroethyl)benzylchloride

Feedstock:

| 15.0 g = | 106.7 mMol 2-phenylethylchloride |
|---|---|
| 4.2 g = | 47.0 mMol 1,3,5-trioxane |
| 5.7 g = | 40.5 mMol phosphorus pentoxide |
| 15.9 g = | 13.8 ml conc. hydrochloric acid |
| 14.7 g = | 8.7 ml o-phosphoric acid 85% |

-continued

| 12.8 ml | acetic acid |
|---|---|

Conducted analogously to example 4.1.

| reaction time: | 20 hours |
|---|---|
| raw product: | 15.8 g |
| vacuum distillation: | 14.8 bar/134° C. lit.: 100° C.–150° C./0.3 mm |
| yield: | 7.4 g = 36.8% of the theoretical yield |

4.3. 4-(3-Chloropropyl)benzylchloride

Feedstock:

| 20.0 g = | 19.1 ml | 129 mMol 3-phenylpropylchloride |
|---|---|---|
| 5.2 g = | | 57 mMol 1,3,5-trioxane |
| 19.2 g = | 16.8 | concentrated hydrochloric acid |
| 17.6 g = | 10.4 ml | o-phosphoric acid 85% |
| 6.8 g | | 49 mMol phosphorus pentoxide |
| | 156.6 ml | concentrated acetic acid |

Conducted analogously to example 4.1.
Yield: 13.0 g = 49.4% of the theoretical yield.

5. Preparation of the compounds of formula VI

5.1. Dimethylaminoacetylbenzylcyanide

Feedstock:
232.4 mMol p-chloroacetylbenzylcyanide 47.0 g
591.8 mMol 40% dimethylamine solution 66.7 g = 75.0 ml
2700.0 ml methanol In a 4 liter round bottomed, four-necked flask 47.0 g of p-chloroacetylbenzylcyanide are dissolved in 2,700 ml of methanol. The solution is cooled to +2° C. in a water ice bath. At this temperature the dimethylamine solution (75.0 ml) is added drop by drop. The reaction mixture is subsequently stirred for ½ hour at +2° C. and then for 24 hours at room temperature. After removal of the volatile components in a rotary evaporator (bath temperature 40° C., water jet vacuum), the oily residue is absorbed in 300 ml 1N hydrochloride acid and 200 ml of distilled water and shaken with a total of 1,100 ml of diethyl ether. The aqueous phase is treated with 450 ml 1N sodium hydroxide solution and 160 g of sodium chloride and extracted with a total of 1,600 ml of diethyl ether. The organic phase is washed to neutrality with water, then dried with sodium sulfate, and concentrated by evaporation in a rotary evaporator (bath temperature 30° C., water jet vacuum).

Yield: 31.1 g = 66.2% of the theoretical yield
p-Chloroacetylbenzylcyanide
Feedstock:

| 766.0 mMol | benzylcyanide | 90 g = 88.2 ml |
|---|---|---|
| 1328.0 mMol | chloroacetylchloride | 150 g = 105.6 ml |
| 2025.0 mMol | aluminum chloride $AlCl_3$ | 270 g |
| 238.2 ml | carbon disulfide $CS_2$ | |

In a 1 liter round bottomed, four-necked flask with condenser, $CaCl_2$ drying tube, pneumatic stirrer and thermometer 88.2 ml of benzylcyanide, 105.6 ml of chloroacetylchloride, and 238.2 ml of carbon disulfide are added. After the solution has been cooled to 0° C., $AlCl_3$ is slowly added. The reaction mixture is heated to 15° C. It is subsequently stirred for another 5 minutes at +2° C., 1.2 hour at room temperature and 2 hours at 40° C. CS₂ is separated and the dark oil is placed on 2.5 kg ice while stirring vigorously. The resulting brown precipitate is filtered by suction over a D4 glass filter funnel, washed with 1N hydrochloric acid, sucked quite dry, and dried in a vacuum drying oven for 18 hours at room temperature. The raw product (104.9 g) is dissolved in boiling 6.4 l i-propanol containing 34 g of activated carbon and then the product is recrystallized upon cooling. After the crystals have precipitated at room temperature, the precipitation is completed. The product is left with the mother liquor for at least 24 hours at 4° C. The white crystals are filtered by suction by means of a D4 glass filter funnel, washed with cold i-propanol and dried in a vacuum drying oven for 18 hours at room temperature.

Yield: 47.0 g=30.2% of the theoretical yield.

Having now fully described the invention, it will be apparent to one of ordinary skill in the art that many changes and modifications can be made thereto without departing from the spirit of scope of the invention as set forth herein.

What is claimed as new and desired to be secured by Letter Patent of the United States is:

1. A pharmaceutically efficacious pteridine compound of formula I

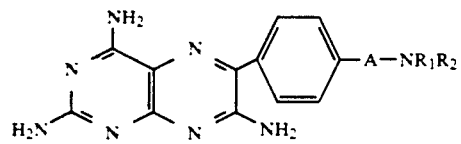

(I)

wherein
A is cycloalkyl or —CR₃R'₃—(CR₃R₄)ₙ—, said —CR₃R'₃— moiety of said group A being directly bonded to the phenyl group of pteridine nucleus;
R₁ is hydrogen, a cycloalkyl group of up to 7 carbon ring atoms, an alkyl group of 1 to 6 carbon atoms or benzyl,
R₂ is hydrogen or an alkyl group of 1 to 6 carbon atoms, or
R₁ and R₂, together with the nitrogen atom to which they are attached, form

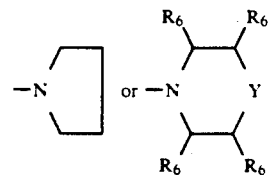

wherein
Y is >CHR₇, —O— or >NR₈
R₆ is hydrogen or alkyl of 1 to 4 carbon atoms, R₇ and R₈ are hydrogen, alkyl of 1 to 6 carbon atoms or benzyl;
R₃ is hydrogen or an alkyl group of 1 to 3 carbon atoms;
R₃' is hydrogen, an alkyl group of 1 to 3 carbon atoms, an alkyl group of 1 to 3 carbon atoms substituted with an OH group or an amino group, a carboxyl group or a hydroxyl group; and
R₄ is hydrogen, C₁₋₄ alkyl, OH or C₁₋₄ alkoxy;
n is 0 or 1 to 7; or
a pharmaceutically acceptable acid addition salt thereof.

2. The compound of claim 1, wherein said salt is an acetate, hydrochloride, hydrobromide, sulfate, citrate, tartrate, succiinate, maleinate, fumarate, lactate or benzoate.

3. The compound of claim 1, wherein A is —CH₂—, —CH(OH)—(CH₂)ₙ— or —C(CH₃)₂—(CH₂)ₙ—, wherein n is 0 or 1 to 7.

4. A pharmaceutical composition comprising a pharmaceutically effective amount of the compound of claim 1 in combination with a pharmaceutically effective carrier.

5. A method of achieving an anti-arrhythmic, cardioprotective, antihypertensive, anti-potassium uretic or diuretic efficacy effect, comprising: administering a therapeutically effective amount of the composition of claim 4 to a subject in need of such effect.

6. The method of claim 5, wherein the dose of active agent ranges from 1 to 100 mg/kg of body weight.

* * * * *